United States Patent [19]

Quirk

[11] Patent Number: 5,017,690

[45] Date of Patent: May 21, 1991

[54] DEBLOCKING N-FORMYL ASPARTAME COMPOUNDS

[75] Inventor: Jennifer M. Quirk, Highland, Md.

[73] Assignee: W. R. Grace & Co.-Conn., New York, N.Y.

[21] Appl. No.: 392,696

[22] Filed: Aug. 11, 1989

[51] Int. Cl.⁵ .................... A61K 37/02; C07C 229/00
[52] U.S. Cl. .................... 530/335; 530/337; 530/801; 560/40; 560/41
[58] Field of Search .......... 530/335, 337, 801; 560/40, 41; 260/112.5

[56] References Cited

U.S. PATENT DOCUMENTS

| | | | |
|---|---|---|---|
| 3,879,372 | 4/1975 | Boesten | 260/112.5 |
| 3,933,781 | 1/1976 | Bachman et al. | 260/112.5 |
| 4,021,418 | 5/1977 | Takemoto et al. | 260/112.5 |
| 4,539,147 | 9/1985 | Filippini et al. | 260/112.5 |
| 4,613,460 | 9/1986 | Casati et al. | 260/112.5 |
| 4,638,081 | 1/1987 | Elefante | 560/41 |
| 4,642,367 | 2/1987 | Finotto | 560/40 |
| 4,656,304 | 4/1987 | Oppici | 560/41 |

OTHER PUBLICATIONS

Gieger et al., CA 50497d, vol. 71 (1969).

*Primary Examiner*—John Doll
*Assistant Examiner*—Bennett Celsa
*Attorney, Agent, or Firm*—Howard J. Troffkin

[57] ABSTRACT

N-formyl amino acid or peptide is deformylated by reaction with aniline or methylene dianiline over noble metal catalyst, e.g., Pt-on-carbon. N-formanilide is formed as by-product. The process is particularly useful in deformylating N-formyl aspartame.

10 Claims, No Drawings

DEBLOCKING N-FORMYL ASPARTAME COMPOUNDS

BACKGROUND OF THE INVENTION (1) Field of the Invention

This invention relates to deblocking N-protected amino acids and peptides, including polypeptides.

(2) Description of the Related Art

A variety of procedures have been used for removing N-protected groups from N-protected amino acids and peptides.

Prior art documentation focusing particularly on processes for deblocking aspartame-type compounds (which is a preferred use of the instant invention) includes:

U.S. Pat. No. 4,539,147 to A. Filippini et al teaches a process for preparing α-L-aspartyl-L-phenylalanine alkyl esters from L-aspartic acid of which the amino group is protected by bonding it to a 3,5-dimethoxy-α,α-dimethhyl-benzyloxycarbonyl group. This reference teaches the removal of the protective group from the final product by the action of U.V. radiation.

In U.S. Pat. No. 3,933,781 to G. L. Bechman, reference is made to various other methods of removing N-protective groups from aspartame type products, inter alia, catalytic hydrogenation and treatment with mineral acids and bases, and within that context specifically, we have an example of the catalytic hydrogenation method.

U.S. Pat. No. 3,879,372 to W. H. J. Boesten which teaches removal of a carbobenzoxy N-protective group by hydrogenation using a palladium catalyst supported on activated carbon. Also, U.S. Pat. No. 4,613,460 to P. Casati et al teaches deprotection of carbobenzoxy protected nitrogen by hydrogenolysis with a palladium-on-carbon catalyst in a glacial acetic environment.

As evident from the foregoing, aspartame is a dipeptide, and as such it is formed with an amide bond between an activated carboxyl group of one amino acid and the amino group of another amino acid. The desired pure peptide requires protection of all other functional groups not involved in the peptide bond formation. Once the final product is isolated and purified, the process of removing the protective groups follows and procedures therefore depend on the type of protective groups used. These commonly are the ones used as N-protectors in peptide chemistry, namely the formyl, acetyl, benzoyl, substituted and unsubstituted carbobenzoxy, t-butoxycarbonyl and the hydrohalide salt groups.

A particularly preferred N-protective group is the formyl group which is used in conjunction with L-aspartic anhydride. French Patent No. 2,040,473, for example, teaches N-formyl-L-aspartic anhydride.

Now, it is very well known that the reaction to remove these N-protective groups is complicated since the splitting of peptidic bonds takes place at the same time with the formation of undesired by-products such as diketopiperazine.

Extensive research therefore has been focused not only on the various synthetic routes for the preparation of aspartame but on the various means to protect the amine group not involved in the peptide bond formation during the synthesis of aspartame and furthermore on the means to bring about de-blocking of said amine groups once the said aspartame compound has been produced and isolated.

When a formyl group is used as a blocking agent for the amine groups not involved in the peptide bond formation of the aspartame synthesis, then de-blocking involves finding a suitable procedure to deformylate the α-L-aspartyl-L-phenylalanine methyl ester sweetener which was synthesized, e.g.,

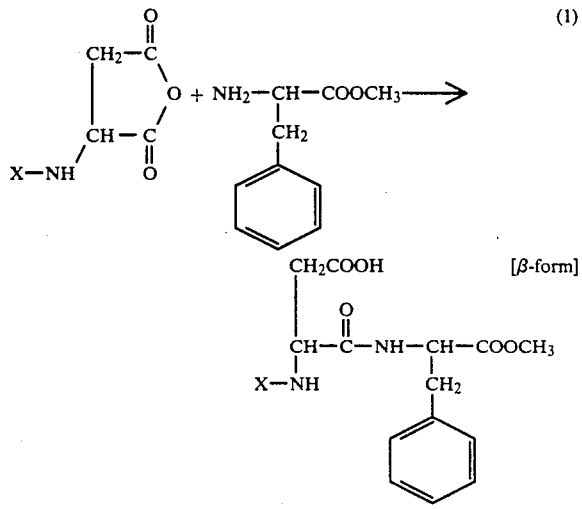

and where X is formyl, HC(:O)—.

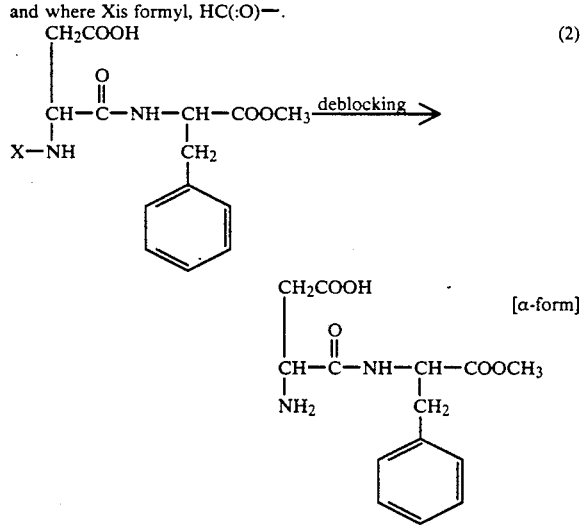

With respect to formyl protected amine groups, deformylation which is the object of the subject invention, is amply documented in the prior art.

One reference for instance, U.S. Pat. No. 4,638,081 to B. Elefante, teaches in a preferred embodiment deformylation through a process comprising use of normal hydrochloric acid in a hydroalcoholic solution under boiling conditions. Another reference, U.S. Pat. 4,642,367 to M. Finotto refers to the use of hydrazine or acylhydrazine in the endeavor to deformylate N-formyl protected α-L-aspartyl-L-phenylalanine methyl esters.

In a variant to the supra approaches, U.S. Pat. No. 4,656,304 to E. Oppici et al teaches the removal of the formyl group directly in the condensation mixture so as to avoid the isolation of N-formyl aspartame and thereby reduce production costs. This reference uses phosphoric acid and a lower alkyl alcohol which are added to the reaction mixture containing N-formyl α-L-aspartyl and β-L-aspartyl-L-phenylalanine methyl ester so that the α-L-aspartyl-L-phenylalanine methyl ester is made to precipitate which is subsequently converted to the free aspartame by treatment with a base.

Other references teach yet additional methods for bringing about deformylation of formyl protected L-aspartyl-L-phenylalanine methyl esters, e.g. U.S. Pat. No. 4,021,418 to T. Takemote et al teaching the use of hydroxylamines in this process.

Disadvantages of the above processes have been pointed out, such as low yields, expensive reagents, esterification of β-carboxy groups and hydrolysis of ester or peptide bonds. Furthermore, deformylation is remarkably affected by concentration and reaction temperatures, particularly when the mineral acid approach is used to bring about this desired deprotective reaction.

OBJECTS OF THE INVENTION

It is an object of the invention to provide a process for deblocking N-formyl protected amino acids, peptides, and polypeptides.

More specifically, it is an object of the subject invention to provide for means to bring about deformylation of N-formyl aspartame.

It is a further object to bring about deformylation of N-formyl aspartame by a process which minimizes formation of diketopiperazine by-product by maximizing aspartame yield at optimum reaction conditions.

The foregoing objects have been accomplished by the provision of novel means of effecting deblocking of N-formyl protected amino acids, peptides, and polypeptides by a process comprising the use of a novel metal catalyst in conjunction with an aniline promoter.

These and other objects of the invention will be further elucidated as the description of the invention proceeds.

BRIEF SUMMARY OF THE INVENTION

An N-formyl amino acid or N-formyl peptide is reacted with aniline or methylene dianiline over a catalyst, e.g., platinum, in a solvent. The aniline accepts the C=O group from N-formyl with formation of N-formanilide. The overall reaction is $$HC(:O)NH-R + \phi-NR'H \xrightarrow{cat.} H_2NR + \phi NR'C(:O)H \quad (I)$$

where R is the residue of an amino acid or peptide as hereinafter defined, $\phi$ is phenyl, and R' is H or $C_{1-10}$ alkyl.

With respect to the preferred embodiment, deformylation of N-formyl aspartame with aniline, the reaction is:

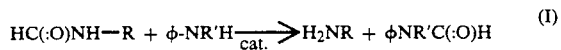

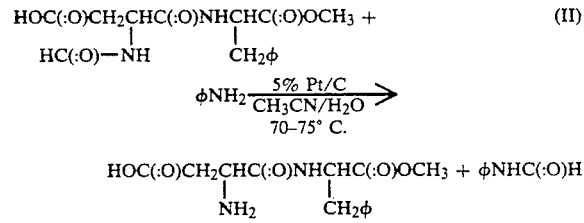

The terms "amino acid", "peptide", and "polypeptide" are used in their conventional senses. Amino acid is a compound containing an amino group (which may be substituted) and a carboxylic acid group (which may be esterified). Peptide and polypeptide refers to a compound comprising moieties of at least two amino acids wherein an amino group of one is condensed with a carboxylic acid group of the other with formation of an amide group. The same condensation may be repeated with production of a polypeptide, which carries an amino group and a carboxyl group. (See definition of "peptide" in H. D. Law, The Organic Chemistry of Peptides, Willy Interscience, 1970, p. 6.) Amino acid residue, peptide residue, and polypeptide residue (cf Equation I above) refers respectively to amino acid, peptide, and polypeptide less the respective amino groups.

DETAILED DESCRIPTION OF THE INVENTION

The present invention is directed to novel means for deblocking N-formyl protected amino acids, peptides, and polypeptides.

A specific embodiment of the invention is based on a novel process for deblocking aspartame, a dipeptide, which may be N-formyl protected during its synthesis.

In the general process, N-formyl amino acid or peptide (including polypeptides) is heated in a solvent in the presence of a catalyst and aniline or methylene dianiline,

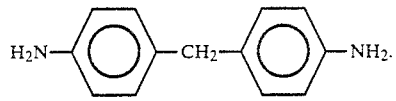

Deformylation begins immediately and ceases in about 4–8 hours. The deformylated product (plus N-formanilide) may be recovered by removing the catalyst, followed by stripping the solvent under reduced pressure. The deformylated product may be separated from N-formanilide by chromatography. Yields may run 30–60% of theory. The mole ratio of amino acid or peptide to aniline or methylene dianiline is not critical; it can vary in the range of 1 mole amino acid or peptide to about 1–10 moles aniline or methylene di-aniline. With regard to catalysts, I greatly prefer platinum and its compounds, e.g. Pt, Pt on carbon, Pt on aluminum, Pt oxides, $H_2PtCl_6$, $PtCl_2$, etc. The amount of catalyst is not critical. Suitably the catalyst metal content is in the range of about 0.1–5 weight % of the N-formyl ingredient. Reaction temperature can be in the range of about 50°–125° C. Suitable solvents include ethanol, toluene, and ethanol acetate. A preferred solvent is acetonitrile/water in a weight ratio 3:1.

Aspartame (APM, L-aspartyl-L-phenylalanine methyl ester) is a white crystalline compound which may be obtained anhydrous, or, more usually, as a half hydrate. When APM is heated it tends to cyclicize to the corresponding diketopiperazine. Accordingly, processes involving APM generally avoid elevated temperatures. Although the process of this invention uses heat, formation of diketopiperazine is kept to a surprising minimum.

With reference to Equation (II) above, approximately 60–70% of the N-formyl aspartame is converted to aspartame, the remaining 30–40% being primarily unreacted N-formyl aspartame and diketopiperazine.

Only runs with aspartame are reported in the following examples. However, the experiments indicate that various analogous ingredients can be used, as follows:

Amino acids: Any suitable N-formyl amino acid. Typical examples include N-formyl glycine, N-formyl alanine, N-formyl serine, N-formyl threonine, N-formyl valine, N-formyl leucine, N-formyl phenyl alanine, N-formyl aspartic acid; N-formyl glutamic acid, and the like.

Peptides (including polypeptides): Peptides and polypeptides useful herein include an suitable N-formylated peptide or polypeptide. Preferred examples include N-formyl-aspartylalanine, N-formylglutamylserine, N-formyl-aspartyl-aspartylglycylserine, etc.

The following examples illustrate without limiting the invention.

Herein, except as otherwise stated, amounts are in percentages by weight.

EXAMPLE 1

To a one-neck round bottom flask equipped with stirring and reflux condenser topped with a nitrogen inlet was added 25 g (0.8 mmol) N-formyl aspartame, 0.35 g (3.8 mmol) aniline, 15 ml acetonitrile, 5 ml water and 100 mg 5% Pt/C (about 2% Pt, based on N-formyl aspartame). The reaction was then heated to 70°-75° C. for 12 hours, after which time it was cool to room temperature. The catalyst was then removed by filtration and the reaction stripped to dryness under vacuum to give a yellow-white gummy solid. $^1$H NMR and HPLC of this solid showed it to contain 55-60% aspartame, with the rest of the material primarily being N-formyl aspartame.

COMPARATIVE EXAMPLE 1

The reaction was run as directed in Example 1, however, no aniline was added. Analysis by $^1$H NMR and HPLC showed that no aspartame had been formed.

EXAMPLE 2

The reaction was run as described in Example 1, however, a reaction temperature of 100° C. was used. Analysis showed that aspartame was formed in 30-35% yield, as well as several other byproducts including diketopiperazine and phenylalanine methyl ester.

EXAMPLE 3

The reaction was run as described in Example 1, however, 0.70 g (7.6 mmol) aniline was used. Analysis of the reaction showed that aspartame was formed in 65-70% yield. Formanilide was also formed.

EXAMPLE 4

The reaction was run as described in Example 1, however, 100 mg PtCl$_2$ was used instead of 100 mg 5% Pt/C. Analysis of the reaction showed that aspartame was formed in 45-50% yield. N-formanilide was also formed.

EXAMPLE 5

The reaction was run as directed in Example 1; however methylenedianiline (0.75 g, 3.8 mmol) was added instead of aniline. A 60% yield of deformylated aspartame was obtained. The weight of Pt metal in the catalyst was about 2% of the N-formyl aspartame.

While the illustrative embodiments of the invention have been described hereinbefore with particularity, it will be understood that various other modifications will be apparent to and can be readily made by those skilled in the art without departing from the scope and spirit of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The embodiments of this invention in which an exclusive property or privilege is claimed are defined as follows.

What is claimed is:

1. A method for removing the formyl group from the nitrogen atom of an N-formyl aspartame compound which comprises heating the N-formyl compound in the presence of a catalytically effective amount of a platinum-containing catalyst in conjunction with a promoting amount of aniline or of methylene dianiline.

2. The method according to claim 1 wherein the catalyst is 5% platinum-on-carbon.

3. The method according to claim 1 wherein the catalyst is platinum chloride.

4. The method according to claim 1 wherein the platinum in the catalyst is in the range of about 0.1-5% of the weight of the N-formyl aspartame compound.

5. The method according to any of claims 1, 2, 3, or 4, wherein the reaction is carried out at 70°-75° C.

6. The method according to claim 1 wherein the N-formyl aspartame compound is N-formyl-L-aspartyl-L-phenylalanine methyl ester.

7. The method according to claim 1, wherein the N-formyl aspartame compound:aniline or methylene dianiline mole ratio is about 1:1-1:10; the catalyst is about 0.1-5% by weight of the N-formyl aspartame compound; the reaction temperature is in the range of about 60°-75° C.; and the reaction is carried out in the presence of a solvent for the N-formyl aspartame compound.

8. The method according to claim 1, comprising reacting N-formyl aspartame compound with aniline in a solvent at about 70°-75° C. for about 12 hours; cooling the reaction mixture; removing the solvent from the mixture under reduced pressure; and recovering a mixture comprising N-formyl aspartame compound and N-formanilide.

9. The method according to claim 8 wherein the N-formyl aspartame compound:aniline mole ratio is about 1:4.75; the catalyst is 5% Pt on charcoal; the catalyst is about 2 weight % of the N-formyl aspartame compound; and the solvent is a 3:1 mixture of acetonitrile:water.

10. The method according to claim 7, wherein the N-formyl aspartame compound:methylene dianiline mole ratio is about 1:4.75, the catalyst is 5% Pt on charcoal; the catalyst is about 2 weight % of the N-formyl aspartame compound; and the solvent is a 3:1 mixture of acetonitrile:water.

* * * * *